(12) United States Patent
Dakin et al.

(10) Patent No.: US 9,427,550 B2
(45) Date of Patent: Aug. 30, 2016

(54) DEVICES AND METHODS FOR DELIVERING VASCULAR IMPLANTS

(71) Applicant: AGA MEDICAL CORPORATION, Plymouth, MN (US)

(72) Inventors: Gregory James Dakin, Minneapolis, MN (US); Darren Todd Prom, Brooklyn Park, MN (US); Anup Dasnurkar, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 380 days.

(21) Appl. No.: 13/771,245

(22) Filed: Feb. 20, 2013

(65) Prior Publication Data

US 2014/0135734 A1    May 15, 2014

Related U.S. Application Data

(60) Provisional application No. 61/724,367, filed on Nov. 9, 2012.

(51) Int. Cl.
*A61M 25/00* (2006.01)
*A61B 17/12* (2006.01)
*A61B 17/00* (2006.01)

(52) U.S. Cl.
CPC .... *A61M 25/0082* (2013.01); *A61B 17/12022* (2013.01); *A61B 2017/00526* (2013.01); *A61B 2017/00623* (2013.01); *A61B 2017/12054* (2013.01); *Y10T 29/49826* (2015.01)

(58) Field of Classification Search
CPC .............. A61M 25/0082; A61M 25/0045; A61M 25/0053; A61M 25/09; A61B 2017/00526; A61B 2017/12054; A61B 2017/00623; A61B 17/12022

USPC .................... 604/508, 164.13, 264, 523, 528
See application file for complete search history.

(56) References Cited

U.S. PATENT DOCUMENTS

| | | |
|---|---|---|
| 4,579,127 A | 4/1986 | Haacke |
| 5,376,083 A | 12/1994 | Mische |
| 5,437,282 A | 8/1995 | Koger et al. |
| 5,932,035 A | 8/1999 | Koger et al. |
| 6,355,027 B1 | 3/2002 | Le et al. |

(Continued)

OTHER PUBLICATIONS

Notification of Transmittal of the International Search Report and the Written Opinion of the International Searching Authority, of the Declaration for International Application No. PCT/US2013/026771 dated Jan. 14, 2014; 14 pages.

(Continued)

*Primary Examiner* — Kami A Bosworth
*Assistant Examiner* — Hamza Darb
(74) *Attorney, Agent, or Firm* — Armstrong Teasdale LLP

(57) ABSTRACT

Embodiments of the present disclosure are directed to delivery devices, methods, and systems for delivering an implant to a target site. In one embodiment, a delivery device includes a core member defining a proximal end and a distal end and an outer winding defining a proximal end and a distal end, wherein the outer winding surrounds and is coupled to the core member. The outer winding extends at least partially between the proximal end of the core member and the distal end of the core member, and the outer winding is configured for displacement within a delivery catheter. The delivery device further includes a coupling member at the distal end of the core member configured to releasably attach to an implant.

18 Claims, 8 Drawing Sheets

(56) References Cited

U.S. PATENT DOCUMENTS

| | | | |
|---|---|---|---|
| 6,589,227 B2 | 7/2003 | Sonderskov Klint | |
| 6,881,194 B2 | 4/2005 | Miyata et al. | |
| 7,507,229 B2 | 3/2009 | Hewitt et al. | |
| 7,905,877 B1 | 3/2011 | Jimenez et al. | |
| 7,909,779 B2 | 3/2011 | Shimogami et al. | |
| 7,951,091 B2 | 5/2011 | Segner et al. | |
| 8,100,881 B2 | 1/2012 | Hoffa | |
| 8,231,551 B2 | 7/2012 | Griffin et al. | |
| 2001/0044633 A1* | 11/2001 | Klint | 606/200 |
| 2005/0027212 A1* | 2/2005 | Segner et al. | 600/585 |
| 2006/0116714 A1* | 6/2006 | Sepetka | A61B 17/12022 606/200 |
| 2007/0123927 A1 | 5/2007 | Farnan | |
| 2007/0123928 A1* | 5/2007 | Farnan | 606/200 |
| 2008/0021408 A1 | 1/2008 | Jacobsen et al. | |
| 2011/0160702 A1 | 6/2011 | Jimenez et al. | |

OTHER PUBLICATIONS

Invitation to Pay Additional Fees and, Where Applicable, Protest Fee (Including Partial International Search Report) for International Application No. PCT/US2013/026771 dated Feb. 20, 2013; 7 pages.
HHS Tube—Fort Wayne Metals [online] [retrieved Sep. 14, 2012]. Retrieved from the Internet: <http://www.fwmetals.com/hhs-wire.php>. (2012), 2 pages.
HHS Tube, Fort Wayne Metals, Research Products Corp., 6.4 (2009), 2 pages.

* cited by examiner

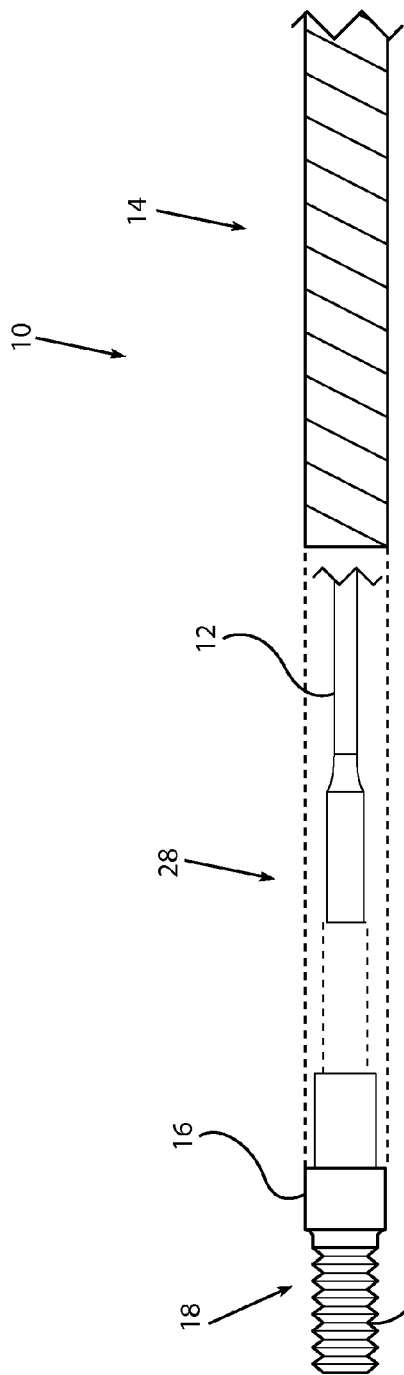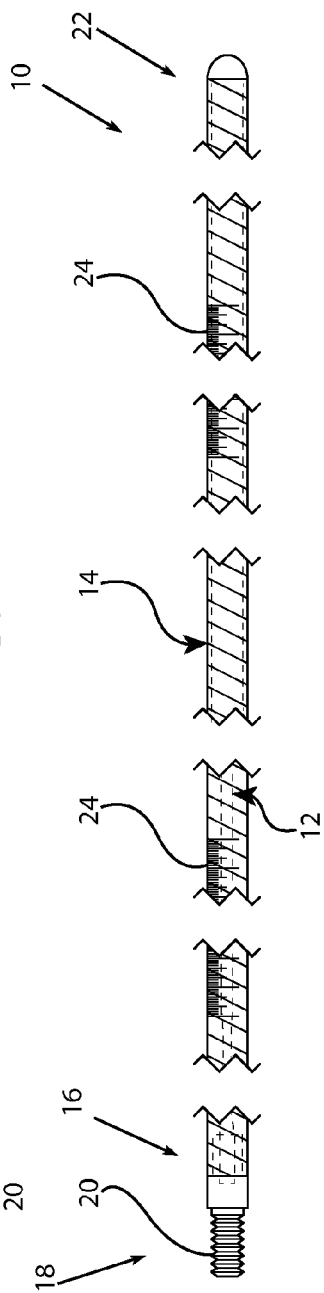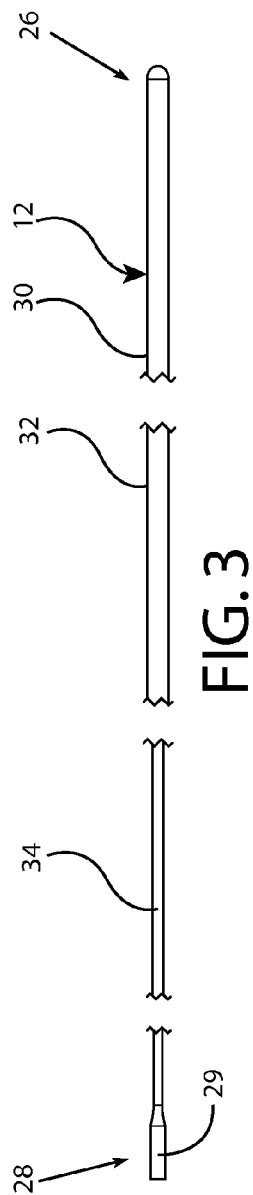
FIG. 1
FIG. 2
FIG. 3

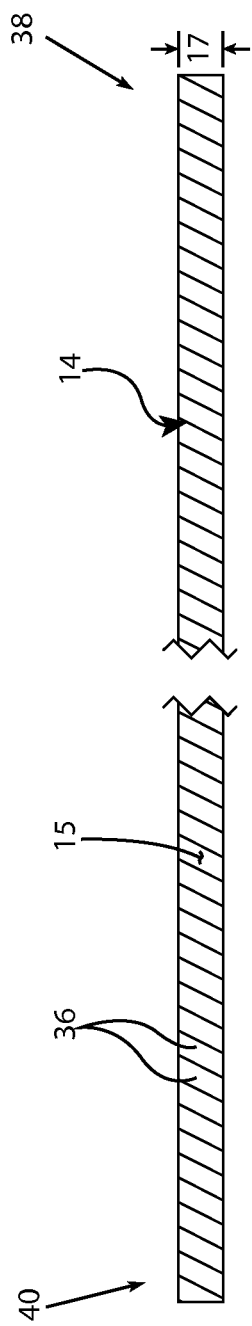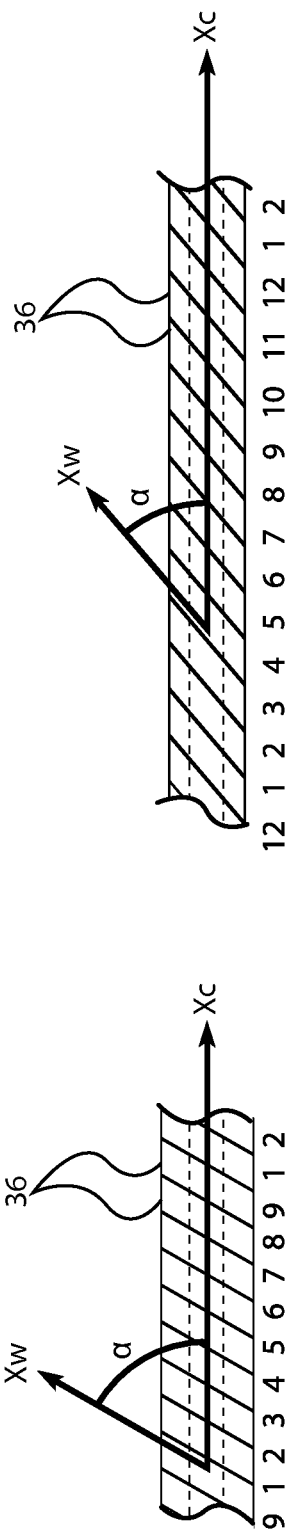

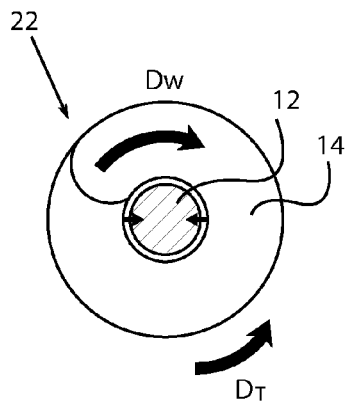
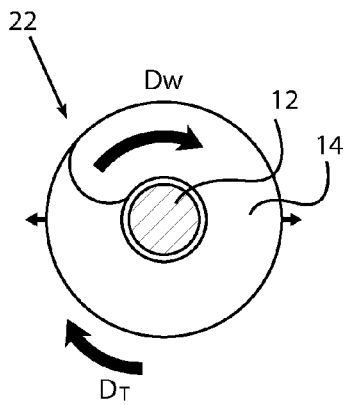
FIG. 10A  FIG. 10B
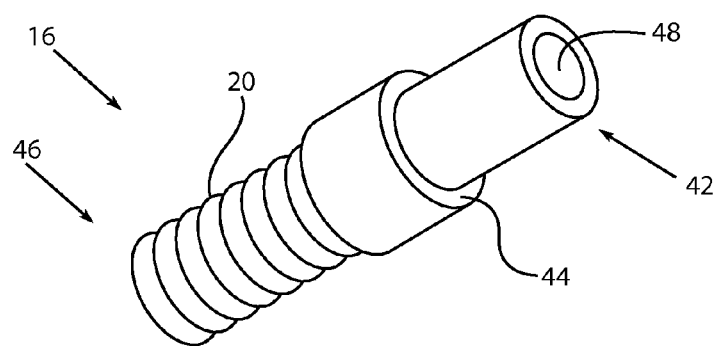
FIG. 11

DEVICES AND METHODS FOR DELIVERING VASCULAR IMPLANTS

CROSS REFERENCE TO RELATED APPLICATIONS

This application claims priority to U.S. Provisional Application No. 61/724,367, filed Nov. 9, 2012, which is incorporated by reference herein in its entirety.

BACKGROUND

I. Field of the Disclosure

The present disclosure relates generally to delivery devices for delivering implants to target sites. More particularly, the present disclosure is directed to devices and methods for delivering vascular implants to areas of a patient's vasculature.

II. Description of the Related Art

Various types of intravascular medical devices, both biological and synthetic, have been used for a large array of reparative vascular procedures, such as to treat obstructive vessels and aneurysms. In some cases, a vascular abnormality occurs in a section of a patient's vasculature that is very narrow and/or in a location in which a tortuous path must be traversed to reach the site intravascularly. For example, when treating vascular abnormalities in the neuro-vasculature, microcatheters having small inner diameters are used. The delivery devices and implants compatible with such microcatheters have correspondingly small diameters to be able to fit inside and traverse the length of the microcatheters. At the same time, the delivery devices are intended to maneuver through small-radius bends and turns in the patient's vasculature.

BRIEF SUMMARY

Embodiments of the present disclosure are directed to delivery devices, methods, and systems for delivering an implant to a target site. In one embodiment, a delivery device includes a core member defining a proximal end and a distal end and an outer winding (e.g., a plurality of wires) defining a proximal end and a distal end, wherein the outer winding surrounds and is coupled to the core member. The outer winding extends at least partially between the proximal end of the core member and the distal end of the core member, and the outer winding is configured for displacement within a delivery catheter. The delivery device further includes a coupling member at the distal end of the core member configured to releasably attach to an implant, wherein the core member and the outer winding are coupled to one another such that a torque applied to a proximal end of the delivery device is transmitted to the coupling member to allow the coupling member to be detached from or attached to the implant.

According to one aspect of the delivery device, the core member and the outer winding each comprises a flexible material. The core member may include a tapered portion at the distal end of the core member. The outer winding may include a uniform maximum inner diameter between the proximal and distal ends thereof, and the outer winding may extend entirely between the proximal and distal ends of the core member. In addition, the proximal and distal ends of the core member may be fixedly attached to the proximal and distal ends of the outer winding, respectively. Respective distal ends of the core member and the outer winding may be fixedly attached to the coupling member. The coupling member may include an engagement member for attaching to and detaching from the implant. Moreover, an inner diameter of the outer winding may approximate an outer diameter of the core member. Each of the wires may be wrapped helically around the core member such that the plurality of wires are compacted and arranged side-by-side to define a single layer.

According to another embodiment of the present disclosure, a delivery device for delivering an implant to a target site is provided. The delivery device comprises a core member defining a proximal end and a distal end and an outer winding comprising a plurality of wires. The plurality of wires surround and are coupled to the core member, and the plurality of wires extend at least partially between the proximal end of the core member and the distal end of the core member. The delivery device also includes a coupling member at the distal end of the core member configured to attach to and detach from an implant in response to manipulation of the delivery device.

In one aspect of the delivery device, each of the wires is wrapped helically around the core member such that the plurality of wires are compacted and arranged side-by-side to define a single layer. The outer winding may include a cold worked outer surface and a swaged outer surface. The outer winding may define an outer surface sized and configured for displacement within a microcatheter having an inner diameter of about 0.03 inches or less. In another aspect, the core member and the outer winding are coupled to one another such that a torque applied to a proximal end of the delivery device is transmitted to the coupling member to allow the coupling member to be detached from, or attached to, the implant. Each of the plurality of wires may define an outer surface having a non-uniform outer diameter taken about a longitudinal axis thereof.

According to another embodiment of the present disclosure, a method of making a delivery device for delivering an implant to a target site is provided. The method comprises providing a core member defining a proximal end and a distal end, wherein the core member comprises a coupling member at the distal end configured to attach to, and detach from, an implant in response to manipulation of the delivery device. The method further includes applying an outer winding having a proximal end and a distal end around the core member at least partially between the proximal end of the core member and the distal end of the core member.

Aspects of the method include reducing an outer diameter of the winding, such as by cold working an outer surface of the winding and/or swaging an outer surface of the winding. A further aspect of the method includes attaching respective distal ends of the core member and the outer winding to the coupling member. The method may also include attaching the proximal and distal ends of the core member to the proximal and distal ends of the outer winding, respectively. Furthermore, the applying step may include applying the outer winding entirely between the proximal and distal ends of the core member. In addition, the applying step may include wrapping a plurality of wires helically around the core member such that the plurality of wires are compacted and arranged side-by-side to define a single layer.

A further embodiment of the present disclosure is directed to a method of delivering an implant. The method includes providing a delivery device, such as according to those embodiments of a delivery device described above. The method also includes attaching the implant to the coupling member of the delivery device and advancing the delivery device and implant through a delivery catheter to the target site. Moreover, the method includes detaching the implant from the coupling member of the delivery device and withdrawing the delivery device and the delivery catheter from the body lumen.

In one aspect, the method further includes recapturing the implant prior to detaching the implant from the coupling member. The attaching step may include rotatably attaching the implant to the coupling member. Likewise, the detaching step may include rotatably detaching the implant from the coupling device. In addition, the advancing step may include advancing the delivery device through a delivery catheter having an inner diameter of about 0.03 inches or less.

According to another embodiment of the present disclosure, a system for delivering an implant to a target site is provided. The system includes a delivery device, such as according to those embodiments of a delivery device described above. The system also includes a delivery catheter configured to receive the delivery device therein such that the delivery device and catheter are axially displaceable with respect to one another. In one aspect, the delivery catheter is a microcatheter having an inner diameter of about 0.03 inches or less.

BRIEF DESCRIPTION OF THE DRAWINGS

The foregoing features and advantages of embodiments in accordance with the present disclosure will become apparent to those skilled in the art from the following detailed description, especially when considered in conjunction with the accompanying drawings in which like numerals in the several views refer to corresponding parts.

FIG. 1 is an enlarged and exploded view of a distal end of a delivery device, illustrating a core member, an outer winding, and a coupling member, according to an embodiment of the present disclosure;

FIG. 2 is a schematic illustration of a delivery device according to an embodiment of the present disclosure;

FIG. 3 is a schematic illustration of a core member of the delivery device from FIG. 2;

FIG. 4 is a schematic illustration of an outer winding of the delivery device from FIG. 2;

FIG. 5A is a schematic illustration of an outer winding having a 9-wire configuration according to one embodiment of the present disclosure;

FIG. 5B is a schematic illustration of an outer winding having a 12-wire configuration according to one embodiment of the present disclosure;

FIG. 10A is a schematic illustration of an outer winding and a core member viewed from a proximal end of a delivery device according to an embodiment in accordance with the present disclosure, where torque is applied in a counter-clockwise direction;

FIG. 10B is a schematic illustration of an outer winding and a core member viewed from a proximal end of a delivery device according to an embodiment in accordance with the present disclosure, where torque is applied in a clockwise direction;

FIG. 11 is a perspective view of the coupling member of the delivery device from FIG. 2;

DETAILED DESCRIPTION

Figure 6:
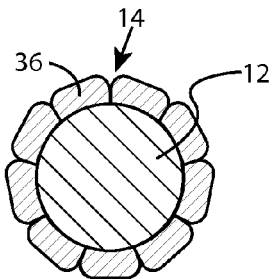
FIG. 6 is a cross-sectional view of a core member and a winding according to one embodiment of the present disclosure.

Conventional delivery devices that are used in connection with microcatheters suffer from several drawbacks. For example, conventional delivery devices are often difficult to connect to implants because both the delivery devices and the implants are small. In order to allow the delivery device to traverse narrow and tortuous sections of a patient's vasculature (e.g., to deliver an implant to a target site in the patient's neuro-vasculature) conventional delivery devices are often configured to be flexible. The flexibility of a conventional delivery device, however, negatively affects the delivery device's ability to advance and retract an implant through a microcatheter. Attaching and detaching the implant to and from the delivery device (e.g., via a threaded attachment) may also be rendered difficult, if not impossible. Moreover, some conventional delivery devices have fluctuations in the outer diameter that result in binding with microcatheters as the delivery devices and microcatheters are displaced with respect to one another.

As described in greater detail below, delivery devices in accordance with the present disclosure are configured to allow torque to be transmitted from one end of the device to the other, while at the same time allowing the delivery device to remain flexible for advancement through a microcatheter to various locations within a patient's vasculature (e.g., neuro-vasculature). Further, the presently disclosed delivery device is configured to facilitate recapture of an implant after deployment from the delivery device. In addition, embodiments of the disclosed delivery device provide a more continuous outer surface to reduce the incidence of binding when displaced within the microcatheter.

The delivery devices and methods described below are generally configured for treating target sites in narrow and/or tortuous portions of a patient's vasculature, such as neuro-vasculature. The delivery devices are generally configured to attach to vascular implants, such as microplugs, for delivery through microcatheters having an inner diameter on the order of 0.030 inches (about 0.762 mm) and smaller, such as the 2.8 French Renegade® microcatheter from Boston Scientific having a 0.027 inch (about 0.686 mm) inner diameter and the 2.7 French Progreat® microcatheter from Terumo Medical Corporation having a 0.025 inch (about 0.635 mm) inner diameter.

It is understood that the use of the term "target site" is not meant to be limiting, as the delivery device may be configured to deliver an implant to any target site, such as an abnormality, a vessel, an organ, an opening, a chamber, a channel, a hole, a cavity, a body lumen, or the like, located anywhere in the body. Although the term "implant" is used, it is understood that the delivery device is configured to deliver any type of medical device to a target site. Moreover, although examples are provided of a delivery device that is used in conjunction with a microcatheter, it is understood that embodiments of the delivery device and methods described herein may be used with other catheters, delivery sheathes, device loaders, and other accessories.

The term "vascular abnormality" is not meant to be limiting, as the delivery device may be configured to deliver an implant for treatment of a variety of vascular abnormalities. For example, the vascular abnormality could be an aneurysm, a rupture, a vessel dissection, or a tumor, among others. Furthermore, the term "lumen" is also not meant to be limiting, as the vascular abnormality may reside in a variety of locations within the vasculature, such as a vessel, an artery, a vein, a passageway, an organ, a cavity, or the like. As also used herein, the term "proximal" refers to a portion of the referenced component of delivery device that is closest to the operator, and the term "distal" refers to a portion that is farthest away from the operator at any given time as delivery device is used to deliver the implant to the target site.

Embodiments of the present disclosure are described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Turning now to the specific embodiments set forth in the accompanying drawings. FIG. 1 depicts one embodiment of delivery device 10, which is configured to deliver an implant through a body lumen to a target site, such as a target site in a patient's neuro-vasculature. Embodiments of delivery device 10 generally comprise core member 12, outer winding 14, and coupling member 16. As illustrated, outer winding 14 surrounds core member 12, while coupling member 16 is disposed at distal end 18 of delivery device 10. Core member 12 and outer winding 14 are coupled to coupling member 16 such that a torque applied to delivery device 10 is transmitted to coupling member 16 to allow coupling member 16 to be detached from and/or attached to the implant (not shown), as described in greater detail below. Coupling member 16 includes an engagement member 20 configured to facilitate such attachment and detachment of the implant.

Outer winding 14 surrounds core member 12 and may extend substantially from proximal end 22 of delivery device 10 to distal end 18 of delivery device 10, as shown in FIG. 2. In some embodiments, markings 24, such as etchings, may be provided on an exterior surface of outer winding 14. Such markings 24 may allow the operator of delivery device 10 to visually determine that delivery device 10 has been properly positioned within a loader device.

FIG. 3 illustrates one embodiment of core member 12 having proximal 26 end and distal end 28. Core member 12 may comprise a flexible material so as to allow delivery device 10 to bend and flex for traversing tortuous sections of a patient's vasculature. In some embodiments, core member 12 may, for example, be a solid wire and may comprise Nitinol or other super elastic or metal alloy material (e.g., stainless steel). To further encourage flexibility of delivery device 10, core member 12 may, in some cases, be gradually tapered toward distal end 28 of core member 12. For example, as shown in FIG. 3, core member 12 may have a uniform diameter along proximal portion 30, between proximal end 26 of core member 12 and mid-section 32 of core member, and tapered portion 34 extending from mid-section 32 to distal end 28 of core member 12. Core member 12 may include engagement member 29 at distal end 28 for facilitating attachment with coupling member 16, as explained in further detail below. For example, engagement member 29 may have a larger diameter than tapered portion 34 and be sized and configured for insertion within coupling member.

Core member 12 may, in some embodiments, have an outer diameter (e.g., along proximal portion 30 and/or mid-section 32) ranging from approximately 0.015 to 0.025 inches (about 0.381 to 0.635 mm), with an outer diameter at distal end 28 of tapered portion 34 ranging from approximately 0.005 to 0.010 inches (about 0.127 to 0.254 mm). In other embodiments, outer diameter of proximal portion 30 may range from about 0.015 to 0.020 inches (about 0.381 to 0.508 mm), 0.017 to 0.022 inches (about 0.432 to 0.559 mm), or 0.020 to 0.025 inches, while outer diameter of tapered portion 34 may range from about 0.005 to 0.007 inches (about 0.127 to 0.178 mm), 0.007 to 0.009 inches (about 0.178 to 0.229 mm), or 0.008 to 0.010 inches (about 0.203 to 0.254 mm).

One factor that affects the flexibility and torque transmission of delivery device 10 includes the diameter of core member 12. In this regard, a larger diameter core member 12 will provide less flexibility than a smaller diameter core member. However, if the diameter of core member 12 becomes too small (especially at distal end 28), torque transmission and tensile strength may be limited. Thus, one advantage provided by the present disclosure is the ability to achieve a balance in providing the smallest diameter core member 12 for placement within a delivery catheter while providing adequate torque transmission, column strength, and tactile feedback during delivery. Proximal portion 30 of core member 12 may include a larger diameter than the tapered portion 34 in order to provide adequate support, while the smaller diameter tapered portion 34 at distal end 28 of core member 12 provides added flexibility.

FIG. 4 illustrates one embodiment of outer winding 14 which defines an outer surface 15 of delivery device 10 having an outer diameter 17. In some embodiments, outer winding 14 comprises a plurality of filars or wires 36, such as, for example, 6 to 16 wires that are arranged in a side-by-side manner and helically wound so as to form a single-layer winding (depending on the number of wires that are used). In one particular embodiment, outer winding 14 includes 9 to 12 wires. In this regard, the ends of a desired number of wires 36 (e.g., 9 wires) may be placed, one adjacent the next, at one end of core member 12 and wrapped together (e.g., as a ribbon or other unitary structure) around core member 12 from proximal end 26 to distal end 28 of core member 12. The greater the number of wires 36 used, the smaller the angle $\alpha$ that results between the longitudinal axis $X_w$ of each wire 36 and the longitudinal axis $X_c$ of core member 12 and winding 14. This is illustrated in FIGS. 5A and 5B, where FIG. 5A shows a 9-wire winding (i.e., 9 wires side-by-side) and FIG. 5B shows a 12-wire winding (i.e., 12 wires side-by-side). In FIGS. 5A and 5B, each wire 36 is labeled with a number (1-9 or 1-12), for purposes of illustration. In other embodiments, winding 14 may include various numbers of wires 36, such as 6 to 8, 6 to 10, 6 to 12, 6 to 14, 7 to 9, 7 to 11, 7 to 13, 7 to 15, 8 to 10, 8 to 12, 8 to 14, 8 to 16, 9 to 11, 9 to 13, 9 to 15, 10 to 12, 10 to 14, 10 to 16, 11 to 13, 11 to 15, 12 to 14, 12 to 16, or 14 to 16 wires 36.

A number of factors may directly affect the flexibility, torque transmission, and variation of the outer diameter of delivery device 10 during delivery of the implant. For example, fewer wires 36 results in more flexibility, less torque transmission, and potentially more variation in the outer diameter (due to separation between individual wires 36 resulting from applied loads), while a larger number of wires 36 (with the same wire diameter and outer diameter 17 of core member 12) provides less flexibility, more torque transmission, and less variation in the outer diameter 17. Likewise, varying the diameter of individual wires 36 affects the flexibility of delivery device 10, as well as the overall diameter of delivery device 10. For instance, larger diameter wires 36 may provide greater torque transmission but will result in a delivery device having a larger outer diameter and less flexibility than smaller diameter wires 36. Thus, one of the advantages provided by the present disclosure is the ability to achieve a balance between the aforementioned factors in order to provide increased flexibility, adequate torque transmission, and minimal variation in the outer diameter 17 of winding 14 with respect to a delivery catheter.

Specific manufacturing techniques may be employed for imparting distinctive structural characteristics to delivery device 10 and limiting the amount of variation in the outer diameter 17 of winding 14 when a torque or other force (e.g., bending, compressive, or tensile load) is applied to delivery device 10. One suitable manufacturing technique is swaging. Swaging, as known to those of ordinary skill in the art, involves a cold working process. In this regard, winding 14 may undergo a swaging process in order to reduce its outer diameter 17 and further compact wires 36 together. Thus, the outer diameter 17 of winding 14 may be reduced or otherwise altered using swaging, cold working, or a similar process. For example, swaging may reduce the outer diameter 17 of winding 14 by up to about 0.003 inches (about 0.076 mm). Swaging may also result in a smoother exterior surface of winding 14 and/or flattening of the exterior surface of winding 14. Thus, rather than wires 36 having a circular cross section, swaging may alter the outer surface of wires 36 to have a non-uniform outer diameter about its longitudinal axis such that each wire 36 has an oblong or non-circular cross-sectional shape, as shown in FIG. 6. By swaging winding 14, wires 36 are also tightly compacted without the need to be attached to one another and have a smooth exterior surface. Tighter compaction of wires 36 and a smoother exterior surface limits variations in the outer diameter 17 of winding 14 as a torque or other force is applied to delivery device 10. Minimizing or eliminating variations in the outer diameter 17 of winding 14 as delivery device 10 is manipulated may reduce the incidence of binding as torque or other force is applied to delivery device 10 and when delivery device 10 is displaced within a delivery catheter since wires 36 will have less tendency to separate from one another. Thus, tighter tolerances between the outer diameter 17 of winding 14 and the inner diameter of the microcatheter can be achieved, while providing sufficient flexibility and torque transmission, as discussed below in reference to FIG. 16.

In some embodiments, wires 36 that form outer winding 14 may comprise a flexible and biocompatible material, such as stainless steel material. Moreover, in one embodiment, winding 14 is a helical hollow strand ("HHS") tube. For example, the HHS tube may be one or more layers of stranded wire formed into a tube with an open core defined therethrough. The HHS can be formed from a variety of materials, such as Nitinol, titanium, stainless steel, and the like. Examples of suitable HHS are those manufactured by Fort Wayne Metals. The inner diameter of winding 14 may, in some cases, approximate the proximal outer diameter of core member 12 (see e.g., FIG. 6). For example, in one embodiment in which the proximal outer diameter of core member 12 is approximately 0.0165 inches (about 0.419 mm), the inner diameter of winding 14 may be approximately 0.0170 inches (about 0.432 mm). Likewise, in an embodiment in which the proximal outer diameter of core member 12 is approximately 0.0170 inches (about 0.432 mm), the inner diameter of winding 14 may be approximately 0.0182 inches (about 0.462 mm), and in an embodiment in which the proximal outer diameter of core member 12 is approximately 0.0175 inches (about 0.445 mm), the inner diameter of outer winding 14 may be approximately 0.0186 inches (about 0.472 mm). Thus, the ratio of the proximal outer diameter of core member 12 to inner diameter of winding 14 may be in a range of between about 0.90 and 0.95. In one embodiment, each wire 36 may have a diameter of about 0.003 to 0.005 inches (about 0.076 to 0.127 mm).

Figure 7:
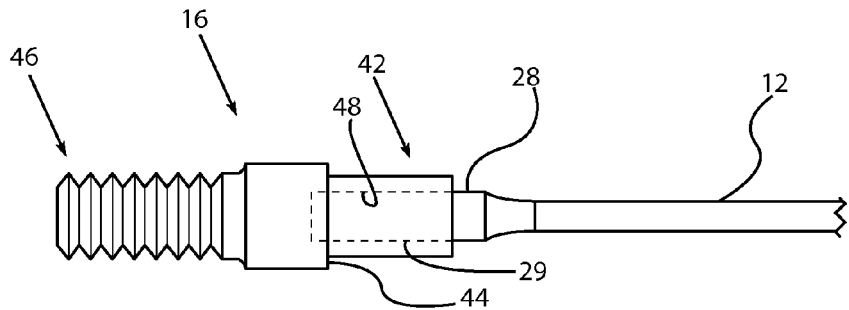
FIG. 7 is a close-up view of a distal end of the delivery device from FIG. 2 with the outer winding removed.
Figure 8:
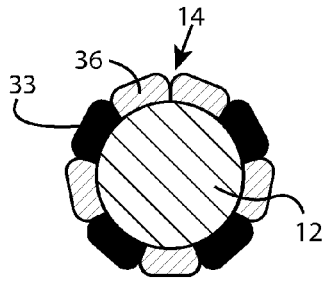
FIG. 8 is a cross-sectional view taken through a mid-section of a delivery device according to one embodiment of the present disclosure.

In some embodiments, delivery device 10 may be constructed such that each end of core member 12 is fixedly attached to a corresponding end of outer winding 14. For example, proximal end 26 of core member 12 and proximal end 38 of outer winding 14 may be welded, adhered, or otherwise fastened to each other. Similarly, distal end 28 of core member 12 and distal end 40 of outer winding 14 may be fixedly attached to each other, such as via coupling member 16. For example, with reference to FIG. 7, engagement member 29 at distal end 28 of core member 12 may be configured to be received within channel 48 defined in proximal end 42 of coupling member 16 and may further be welded or otherwise fixed to coupling member 16. Distal end 40 of outer winding 14 may, in turn be welded or otherwise fixedly attached to proximal end 42 of coupling member 16, which may thus serve to fixedly attach outer winding 14 to core member 12. For example, in one embodiment shown in FIG. 7, coupling member 16 may include transverse surface 44 at its proximal end 42 to which outer winding 14 (e.g., each wire 36 forming the outer winding) may be welded, such as via laser bend welding. Thus, core member 12 and winding 14 may be attached to one another only at their respective proximal and distal ends. In other embodiments, winding 14 and core member 12 may be also attached at one or more locations between proximal 26 and distal 28 ends of core member 12. For example, winding 14 and core member 12 may be welded or otherwise fixed to one another at one or more locations between proximal 26 and distal 28 ends of core member 12. In one embodiment, winding 14 and core member 12 are attached to one another about mid-section 32 of core member 12, such as with one or more spot welds 33 spaced about the circumference of core member 12, as shown in FIG. 8.

Figure 9:
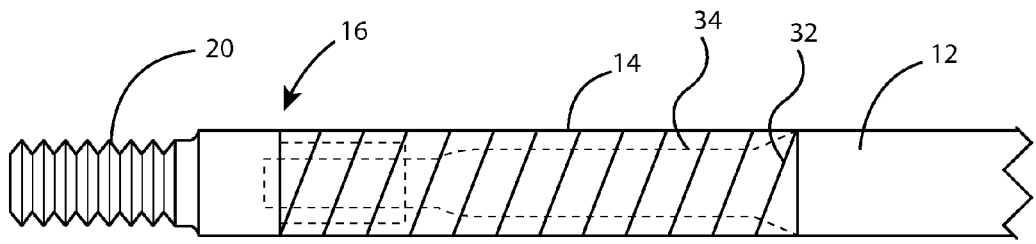
FIG. 9 is a schematic illustration of a delivery device according to another embodiment of the present disclosure.

Winding 14 may extend completely between proximal 26 and distal 28 ends of core member 12. For example, FIG. 2 illustrates core member 12 in relation to winding 14 (shown in hidden lines for purposes of illustration). In one embodiment, the outer diameter of core member 12 is varied along its length and outer winding 14 comprises a uniform maximum inner diameter between proximal 38 and distal 40 ends thereof. In this instance, the inner diameter of winding 14 may be closely matched to the outer diameter of core member 12 at the proximal end 26, while there may be a gap defined between the inner diameter of winding 14 and tapered portion 34 of core member 12 at distal end 28, as shown in FIG. 2. In other embodiments, winding 14 extends along a portion of core member 12 between proximal 26 and distal 28 ends of core member 12. For instance, winding 14 may only extend over tapered portion 34 of core member 12 proximate distal end 28 of core member 12, as shown in FIG. 9. In this case, winding 14 may be attached to core member 12 such that the outer diameter of winding 14 matches the outer diameter of core member 12 at a proximal end of tapered portion 34. With reference to FIG. 9, the outer diameter of winding 14 is approximately the same as the outer diameter of the core member 12. In this way, a consistent outer diameter is provided between proximal 22 and distal 18 ends of delivery device 10.

As discussed above, the connection between core member 12 and winding 14 provides the requisite torque transmission for attaching and detaching the implant. With reference to FIG. 10A, wires 36 of outer winding 14 may be wound in a clockwise direction ($D_w$) when viewed from proximal end 22 of delivery device 10 going into the page to favor torque transmission in the counterclockwise direction. In this way, as proximal end 38 of outer winding 14 and proximal end 26 of core member 12 are turned in a counterclockwise direction $D_T$ (e.g., via application of torque to proximal end 22 of delivery device 10), torque is transmitted from proximal end 22 of delivery device 10 to distal end 18 of delivery device 10, where coupling member 16 will in turn rotate in the counterclockwise direction to disengage from, or engage with, the implant. For example, when coupling member 16 includes right-handed external threads, the scenario depicted in FIG. 10A would cause coupling member 16 to disengage from (e.g., unscrew from) the threads of the implant.

If torque is applied to proximal end 22 of delivery device 10 in the clockwise direction $D_T$, as shown in FIG. 10B, the torque is transmitted from proximal end 22 of the delivery device 10 toward distal end 18 and coupling member 16. In this way, coupling member 16 may be rotated in the clockwise direction so as to, for example, allow coupling member 16 to engage with, or disengage from, the implant. For example, when coupling member 16 includes right-handed external threads, the scenario depicted in FIG. 10B would cause coupling member 16 to engage with (e.g., screw onto) the threads of the implant, so as to tighten the engagement between the corresponding threads. Although the transmission of torque may be more efficient in the scenario described with respect to FIG. 10A (due to the clockwise winding of outer winding 14 to facilitate disengagement of coupling member 16 from an attached implant), an adequate amount of torque may also be transmitted in the detaching scenario of FIG. 10B.

Figure 12:
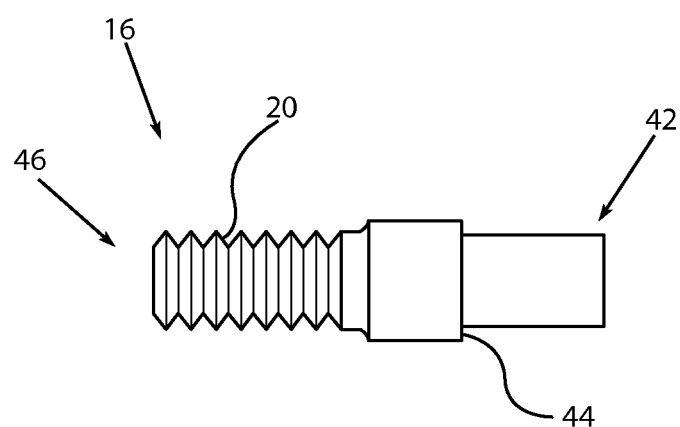
FIG. 12 is a side view of the coupling member from FIG. 11.
Figure 13:
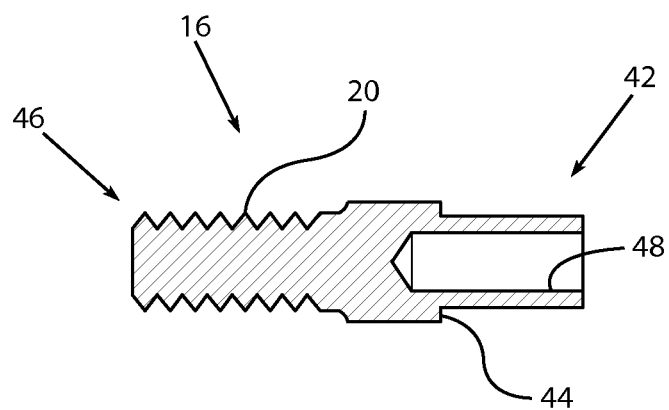
FIG. 13 is a cross-sectional side view of the coupling member from FIG. 11.

One embodiment of coupling member 16 is shown in greater detail in FIGS. 11-13. With reference to FIGS. 11-13, proximal end 42 of coupling member 16 may define channel 48 configured to receive distal end 28 of core member 12. Coupling member 16 is configured to attach to distal end 28 of core member 12 via channel 48, as illustrated in FIG. 7 and described above. For example, distal end 28 of core member 12 may be cylindrical, and channel 48 defined by proximal end 42 of coupling member 16 may also be cylindrical and may have an inner diameter that approximates the outer diameter of distal end 28 of core member 16, such that distal end 28 of core member 16 fits within and engages coupling member 16 via channel 48. In some cases, channel 48 and distal end 28 of core member 12 may have other cross-sectional shapes configured to engage one another, and core member 12 may be welded, adhered, or otherwise permanently fixed to coupling member 16 upon receipt within channel 48.

Distal end 46 of coupling member 16 may, in turn, be configured to releasably attach to the implant, as noted above. For example, distal end 46 of the coupling member 16 may comprise engagement member 20, such as external threads, configured to engage corresponding internal threads of the implant. In this way, the implant may be attached to delivery device 10 for delivery to the target site via engagement with engagement member 20 of coupling member 16. Accordingly, a torque applied to proximal end 22 of delivery device 10 that is transmitted to coupling member 16 may allow coupling member 16 to be threaded into and out of engagement with the implant, depending on the direction in which the torque is applied, as described above. Other suitable techniques may be used to engage and disengage coupling member 16 from the implant in response to manipulation of delivery device 10 while providing the ability to transmit torque, such as a press fit, snap fit, twist-fit, and the like.

A method for making a delivery device for delivering an implant to a target site as described above is summarized in FIG. 14. The method includes providing a core member defining a proximal end and a distal end (Block 200) and applying an outer winding around the core member at least partially between the proximal end of the core member and the distal end of the core member (Block 210). In applying the outer winding around the core member, the outer winding could be formed separately and the core member inserted therein, or the wires may be wound about the core member. The outer diameter of the winding may be reduced (Block 213) such as by cold working (Block 215) and/or swaging (Block 217) as discussed above, and the winding and core member may be attached to one another at one or more locations (Block 219). A coupling member may be attached to the distal end of the core member, where the coupling member is configured to releasably attach to an end of the implant to be delivered to the target site. Block 220. For example, as described above with reference to the figures, the core member and the outer winding may be welded to each other at their respective proximal ends, and the core member and the outer winding may be fixedly attached to each other via attachment (e.g., welding) to the coupling member at their respective distal ends.

As detailed above, the core member and the outer winding may be configured such that a torque applied to the proximal end of the delivery device is transmitted to the coupling member to allow the coupling member to be detached from or attached to the implant. In some embodiments, for example, the delivery device may have an overall length between about 35 and 75 inches (about 90 and 191 cm) and an overall diameter of between about 0.019 and 0.029 inches (about 0.483 and 0.737 mm). In other embodiments, the outer diameter of the delivery device is between about 0.019 and 0.021 inches (about 0.483 and 0.533 mm), about 0.019 and 0.023 inches (about 0.483 to 0.584 mm), about 0.019 and 0.025 inches (about 0.483 and 0.635 mm), about 0.019 and 0.027 inches (about 0.483 and 0.686 mm), about 0.020 and 0.022 inches (about 0.508 and 0.559 mm), about 0.020 and 0.024 inches (about 0.508 and 0.610 mm), about 0.020 and 0.026 inches (about 0.508 and 0.660 mm), about 0.020 and 0.028 inches (about 0.508 and 0.711 mm), about 0.022 and 0.024 (about 0.559 and 0.610 mm), about 0.022 and 0.026 inches (about 0.559 and 0.660 mm), about 0.022 and 0.028 inches (about 0.559 and 0.711 mm), about 0.024 and 0.026 inches (about 0.610 and 0.660 mm), about 0.024 and 0.028 inches (about 0.610 and 0.711 mm), or about 0.026 and 0.028 inches (about 0.660 and 0.711 mm). Accordingly, the resulting delivery device may be used for delivering implants, such as microplugs and other implantable medical devices, through microcatheters having an inner diameter between about 0.02 to 0.03 inches (about 0.51 to 0.76 mm).

Figure 15:
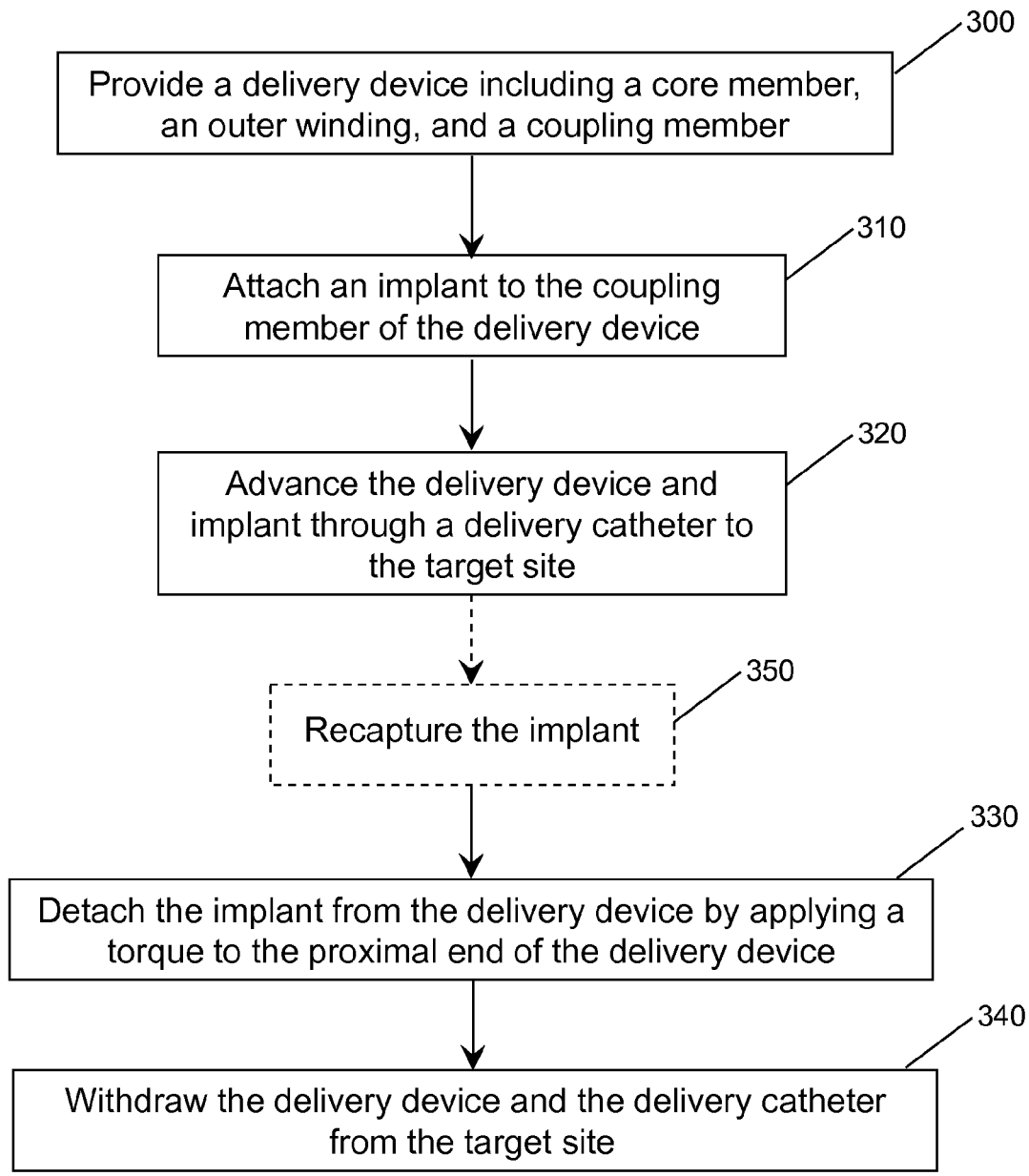
FIG. 15 is a flowchart illustrating a method of delivering an implant according to an embodiment of the present disclosure.

In FIG. 15, a method for delivering a medical device, such as an implant, as described above is summarized. The method includes providing a delivery device configured as described above in connection with one or more of FIGS. 1-13. Block 300. For example, the delivery device may include a core member defining a proximal end and a distal end, an outer winding surrounding the core member and extending at least partially between the proximal end of the core member and the distal end of the core member, and a coupling member attached to the distal end of the core member. The coupling member may be configured to attach and detach to an end of the implant.

At Block 310, the implant may be attached to the coupling member of the delivery device. Attachment of the implant may occur, in some cases, at a facility at which the delivery device is manufactured, such that an operator of the delivery device receives the delivery device and the implant already attached. Alternatively, the implant may be attached to the delivery device at the time of use or implantation or at a separate location from where the delivery device is manufactured. The delivery device and the implant may then be advanced through a delivery catheter, such as a microcatheter, to the target site at Block 320. The implant may then be detached from the delivery device at Block 330 by applying a torque to the proximal end of the delivery device, and the delivery device and the delivery catheter may be withdrawn from the target site at Block 340. In some cases, at Block 350, the implant may be recaptured by retracting the implant relative to the delivery catheter prior to detaching the implant (Block 330), such as in cases where the implant is to be repositioned (e.g., when the implant is deployed in an incorrect location or could be more favorably positioned).

Figure 16:
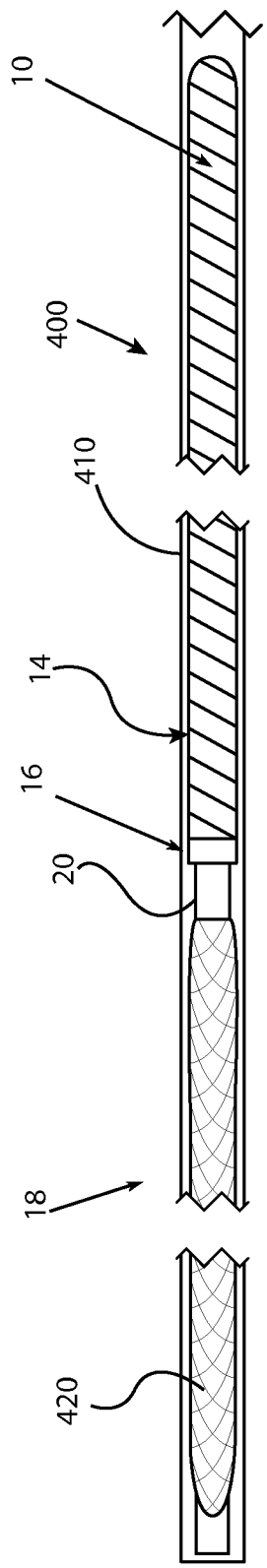
FIG. 16 is a schematic illustration of a system for delivering an implant according to an embodiment of the present disclosure.

FIG. 16 illustrates one embodiment of a system for delivering an implant through a body lumen to a target site. In this regard, system 400 comprises delivery catheter 410 for delivering implant 420. In one example, delivery catheter 410 is a microcatheter as discussed above. Delivery device 10 is disposed in delivery catheter 410 and is configured to be axially displaceable with respect to delivery catheter 410. As noted above, delivery device 10 is configured to minimize or eliminate variations in the outer diameter of winding 14 as delivery device 10 is manipulated so as reduce the incidence of binding as torque or other force is applied to delivery device 10 and when delivery device 10 is displaced within delivery catheter 410. Engagement member 20 is coupled to implant 420 and configured to facilitate such attachment to and detachment from implant 420. In addition, delivery catheter 410 and delivery device 10 are configured to be displaced with respect to one another to deploy implant 420 at a target site.

In some cases, a loader device may be used to facilitate entry of the delivery device and the implant into the microcatheter, which may already be disposed within the body lumen. In this regard, the loader device may be passed over the proximal end of the delivery device, and the delivery device may be pulled proximally such that distal portions of the delivery device move through the loader device.

The distal end of the loader device may, in turn, be configured to engage the proximal end of the delivery catheter (e.g., the microcatheter) disposed within the body lumen. Once engaged, the delivery device (and attached implant) may be advanced through the loader device and the delivery catheter to the target site for delivery of the implant. Once the loader device is engaged with the delivery catheter and the delivery device is advanced distally out of the loader device and into the delivery catheter, the markings may further allow the operator to visually determine that the delivery device has been adequately advanced into the delivery catheter to allow the loader device to be removed from the delivery catheter without causing kinking or other damage to the delivery device.

Figure 14:
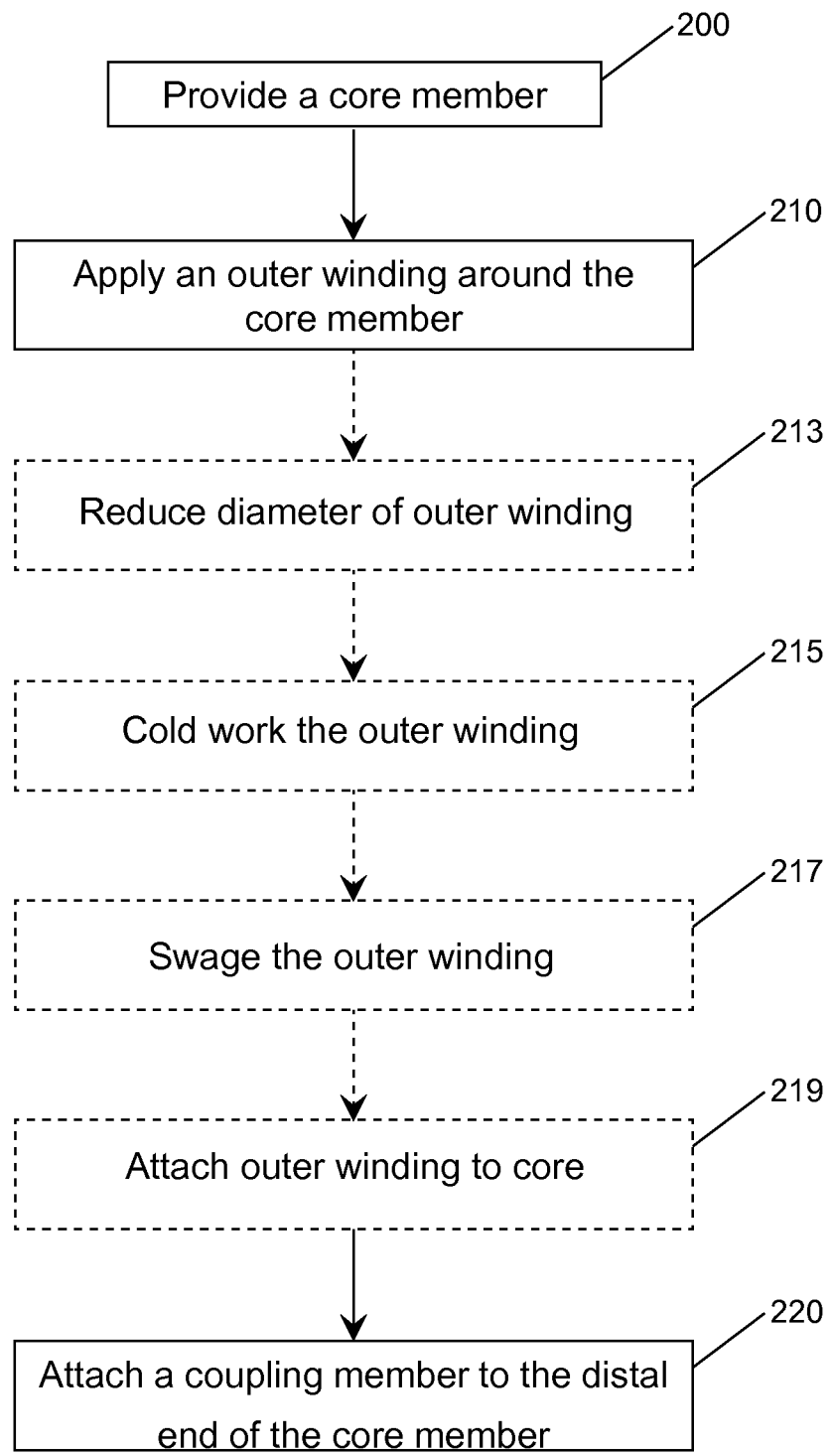
FIG. 14 is a flowchart illustrating a method for making a delivery device for delivering an implant to a target site according to an embodiment in accordance with the present disclosure.

The method depicted in FIG. 14 and described above represents only one possible method for making a delivery device for delivering an implant to a target site. Similarly, the method depicted in FIG. 15 and described above represents only one possible method for delivering an implant. It is understood that the illustrated steps in FIGS. 13 and 14 may be performed in any desired order and should not be limited to the illustrated embodiments. In some embodiments, certain ones of the steps described above may be modified, omitted, or further amplified. Furthermore, in some embodiments, additional optional steps may be included, some examples of which are shown in dashed lines in FIGS. 14 and 15. Modifications, additions, omission, or amplifications to the steps above may be performed in any order and in any combination. The particular methods of manufacturing and delivery will depend on the desired configuration of the delivery device, the patient's anatomy, the condition and location of the target site, the preferences of the practitioner, and/or other considerations.

A delivery device configured according to the embodiments described above provides for several advantages over conventional delivery devices. For example, embodiments of the outer winding resist kinking even under radial loading of the delivery device that may occur as a result of buckling of the microcatheter during delivery and/or recapture of the implant. Furthermore, embodiments of the outer winding configured as described above exhibit minimal stiffness to allow for enhanced distal flexibility, facilitating the traversal of tortuous portions of the vasculature. Embodiments of the outer winding also provide a tight tolerance to limit radial movement between the surface of the delivery device and the microcatheter through which it is advanced. Moreover, embodiments of the disclosed delivery device provide a more continuous outer surface to reduce the incidence of binding when displaced within the microcatheter. In addition, a core member according to the embodiments described above provides the delivery device with a balance of flexibility and structural support, while also allowing an operator of the delivery device to receive adequate tactile feedback during advancement and maneuvering of the delivery device. Although the examples and embodiments described above are with reference to a delivery device that may be used in connection with a microcatheter, embodiments of the delivery device may be used for contrast injection through a diagnostic catheter while the delivery device is still attached to the implant. For example, the disclosed delivery device may be configured to be delivered through a 4 French diagnostic catheter or a 0.038 inch (0.965 mm) guidewire compatible diagnostic catheter.

Many modifications and other embodiments of the disclosure set forth herein will come to mind to one skilled in the art to which these embodiments pertain having the benefit of the teachings presented in the foregoing descriptions and the associated drawings. Therefore, it is to be understood that the above-described embodiments are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A delivery device for delivering an implant to a target site, the delivery device comprising:
    a core member defining a proximal end and a distal end;
    an outer winding defining a proximal end and a distal end, the outer winding surrounding and coupled to the core member, the outer winding extending at least partially between the proximal end of the core member and the distal end of the core member, the outer winding configured for displacement within a delivery catheter; and
    a coupling member fixedly attached to each of the distal end of the core member and the distal end of the outer winding and configured to releasably attach to an implant, wherein the core member and the outer winding are coupled to one another such that a torque applied to a proximal end of the delivery device is transmitted to the coupling member to allow the coupling member to be detached from, or attached to, the implant.

2. The delivery device of claim 1, wherein the core member and the outer winding each comprises a flexible material.

3. The delivery device of claim 1, wherein the outer winding comprises a plurality of wires.

4. The delivery device of claim 3, wherein an inner diameter of the outer winding approximates an outer diameter of the core member.

5. The delivery device of claim 3, wherein each of the wires is wrapped helically around the core member such that the plurality of wires are compacted and arranged side-by-side to define a single layer.

6. The delivery device of claim 1, wherein the core member comprises a tapered portion at the distal end of the core member.

7. The delivery device of claim 6, wherein the outer winding comprises a uniform maximum inner diameter between the proximal and distal ends thereof.

8. The delivery device of claim 1, wherein the outer winding extends entirely between the proximal and distal ends of the core member.

9. The delivery device of claim 8, wherein the proximal and distal ends of the core member are fixedly attached to the proximal and distal ends of the outer winding, respectively.

10. The delivery device of claim 1, wherein the coupling member comprises an engagement member for attaching to and detaching from the implant.

11. A system for delivering an implant to a target site, the system comprising:
    a delivery device comprising:
        a core member defining a proximal end and a distal end;
        an outer winding defining a proximal end and a distal end, the outer winding surrounding and coupled to the core member, the outer winding extending at least partially between the proximal end of the core member and the distal end of the core member; and
        a coupling member fixedly attached to each of the distal end of the core member and the distal end of the outer winding and configured to releasably attach to an implant, wherein the core member and the outer winding are coupled to one another such that a torque applied to a proximal end of the delivery device is transmitted to the coupling member to allow the coupling member to be detached from, or attached to, the implant; and
    a delivery catheter configured to receive the delivery device therein such that the delivery device and catheter are axially displaceable with respect to one another.

12. The system of claim 11, wherein the delivery catheter is a microcatheter having an inner diameter of about 0.03 inches or less.

13. The system of claim 12, wherein each of the plurality of wires is wrapped helically around the core member such that the plurality of wires are compacted and arranged side-by-side to define a single layer.

14. The system of claim 12, wherein each of the plurality of wires defines an outer surface having a non-uniform outer diameter taken about a longitudinal axis thereof.

15. The system of claim 11, wherein the outer winding comprises a plurality of wires.

16. The system of claim 11, wherein the outer winding extends entirely between the proximal and distal ends of the core member.

17. The system of claim 11, wherein the proximal and distal ends of the core member are fixedly attached to the proximal and distal ends of the outer winding, respectively.

18. The system of claim 11, wherein the coupling member comprises an engagement member for attaching to, and detaching from, the implant.

* * * * *